(12) United States Patent
Flohr et al.

(10) Patent No.: US 7,019,001 B2
(45) Date of Patent: Mar. 28, 2006

(54) SUBSTITUTED BENZOTHIAZOLE AMIDE DERIVATIVES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 63 days.

(21) Appl. No.: 10/691,770

(22) Filed: Oct. 23, 2003

(65) Prior Publication Data
US 2004/0229893 A1    Nov. 18, 2004

Related U.S. Application Data

(62) Division of application No. 10/308,338, filed on Dec. 3, 2002, now Pat. No. 6,727,247.

(30) Foreign Application Priority Data
Dec. 10, 2001   (EP) ................... 01129228

(51) Int. Cl.
*A61K 31/5377*   (2006.01)
*C07D 413/02*    (2006.01)

(52) U.S. Cl. ............ 514/233.8; 544/106; 544/135; 546/184; 546/192; 546/198; 514/231.2; 514/315; 514/321

(58) Field of Classification Search ........ 544/106, 544/135; 546/184, 192, 198; 514/231.2, 514/233.8, 315, 321
See application file for complete search history.

(56) References Cited

U.S. PATENT DOCUMENTS

| | | | |
|---|---|---|---|
| 3,954,766 A | 5/1976 | Henry et al. | |
| 6,521,754 B1 * | 2/2003 | Alanine et al. | 544/129 |
| 6,599,901 B1 * | 7/2003 | Flohr et al. | 514/233.8 |
| 6,727,247 B1 * | 4/2004 | Flohr et al. | 514/235.2 |
| 6,835,732 B1 * | 12/2004 | Alanine et al. | 514/235.5 |
| 2002/0045615 A1 | 4/2002 | Alanine et al. | |

FOREIGN PATENT DOCUMENTS

| EP | 0 113 219 | 7/1984 |
|---|---|---|
| WO | WO 01/57008 | 8/2001 |
| WO | WO 01/97786 | 12/2001 |

OTHER PUBLICATIONS

Masahiko, Okada, et al. *Journal of Polymer Science: Part A: Polymer Chemistry*, vol. 28, pp. 3251-3260 (1990).
Poulsen et al., *Bioorganic & Med. Chem.*, vol. 6, pp. 619-641 (*1998*).
Muller et al., *Bioorganic & Med. Chem.*, vol. 6, pp. 707-719 (*1998*).
Kim et al., *J. Med. Chem.*, vol. 41, pp. 2835-2845 (*1998*).
Li et al., *J. Med. Chem.*, vol. 41, pp. 3186-3201 (*1998*).
Baraldi et al., *J. Med. Chem.*, vol. 41, pp. 2126-2133 (*1998*).
Li et al., *J. Med. Chem.*, vol. 42, pp. 706-721 (*1999*).
Baraldi et al., *J. Med. Chem.*, vol. 39, pp. 1164-1171 (*1996*).
Colotta et al., *Arch. Pharm. Med. Chem.*, vol. 332, pp. 39-41 (*1999*).
Domoki et al., *Am. J. Physiol.*, vol. 276, pp. H1113-H1116 (*1999*).
Haas et al., *Naunyn Schniedeberg's Arch. Pharmacol.*, vol. 362, pp. 375-381 (*2000*).
Dionisotti et al., *British Journal of Pharmacology*, vol. 121, pp. 353-360 (*1997*).
MacTavish et al., *J. Chem. Soc., Perkin Trans. 1*, 1996, vol. 20, pp. 2545-2551.

* cited by examiner

*Primary Examiner*—Golam M. M. Shameem
(74) *Attorney, Agent, or Firm*—George W. Johnston; Patricia S. Rocha-Tramaloni; Kimberly J. Prior

(57) ABSTRACT

A compound of formula I and a method of treatment of diseases, related to modulation of the adenosine $A_2$ receptor system comprising administering a compound of formula

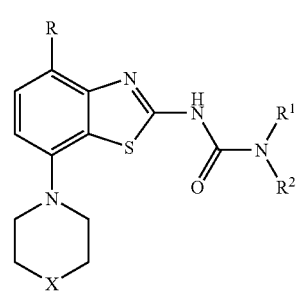

I to a person in need of such treatment.

9 Claims, No Drawings

SUBSTITUTED BENZOTHIAZOLE AMIDE DERIVATIVES

PRIORITY TO RELATED APPLICATIONS

This application is a Division of Ser. No. 10/308,338, filed Dec. 3, 2002 now U.S. Pat. No. 6,727,247.

FIELD OF INVENTION

The present invention is directed to the use of adenosine receptor ligands in a method of treatment, control, or prevention of central nervous system disorders.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers.

Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricular arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treament of diabetes mellitus and obesity.

The current knowledge on adenosine receptors is summarized in various documents including, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

Additionally, WO 01/57008 describes benzothiazolyl urea derivatives and their use as protein kinase inhibitors. According to WO 01/57008, compounds are useful as inhibitors of tyrosine kinases that are important in hyperproliferative diseases, especially in cancer and in the process of angiogenesis. The compounds of formulae IA and IB below are not encompassed by WO 01/57008.

SUMMARY OF THE INVENTION

The present invention is directed to a method of treatment of diseases related to modulation of the adenosine $A_2$ receptor comprising administering a therapeutically effective amount of a compound of formula

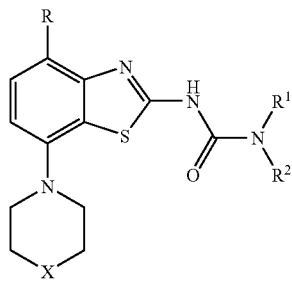

I wherein
R is lower alkoxy or halogen;
$R^1/R^2$ are independently selected from the group consisting of hydrogen, lower alkyl, tetrahydropyran-4-yl and cycloalkyl, said cycloalkyl being unsubstituted or substituted by one or two substituents, selected from the group consisting of
  halogen, lower alkoxy and hydroxy, or
$R^1$ and $R^2$, together with the N atom to which they are attached, form a heterocyclic ring, selected from the group consisting of
  2-oxa-5-aza-bicyclo[2.2.1]heptane,
  3-endo-hydroxy-8-aza-bicyclo[3.2.1]octane,
  2-aza-bicyclo[2.2.2]octane,
  1-oxo-2,8-diaza-spiro[4.5]decane,
  3-aza-spiro[5.5]undecane,
  8-aza-spiro[4.5]decane,
  1-oxa-8-aza-spiro[4.5]decane,
  1,8,8-trimethyl-3-aza-bicyclo[3.2.1]octane,
  [1,4]oxazepane,
  2-oxa-5-aza-bicyclo[2.2.2]octane,
  8-oxa-3-aza-bicyclo[3.2.1]octane,
  1,4-diaza-bicyclo[3.2.1]octane,
  2-aza-bicyclo[2.2.1]heptane, and
  3-aza-bicyclo[3.2.1]octane, said heterocyclic ring being unsubstituted or substituted by lower alkyl, or
piperazinyl, said piperazinyl being unsubstituted or having one or two substituents selected from the group lower alkyl, phenyl and oxo or piperidin-1-yl, substituted by a substituent selected from the group —$(CH_2)_n$—NR'S(O)$_2$-lower alkyl, —C(O)NR'$_2$ and —$(CH_2)_n$-phenyl, said phenyl ring being unsubstituted or substituted by lower alkyl and R' is independently selected from the group hydrogen and lower alkyl;
X is —O— or —$CH_2$—; and
n is 0, 1, 2, 3 or 4
or a pharmaceutically acceptable acid addition salt thereof to a patient in need of such treatment.

Diseases modulated by antagonist activity at the adenosine $A_2$ receptor include Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Additionally, a therapeutically effective amount of a compound of formula I of the present invention may be administered as a sedative, muscle relaxant, antipsychotic, antiepileptic, anticonvulsant and cardioprotective agent for disorders such as coronary artery disease and heart failure.

The most preferred indications in accordance with the method of treatment of the present invention present invention are those, modulated by $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

It has surprisingly been found that the compounds of formula I are adenosine receptor ligands. Specifically, the compounds of the present invention have a good affinity to the $A_{2A}$-receptor and a high selectivity to the $A_1$- and $A_3$ receptors.

The present invention also relates to novel compounds of formula IA

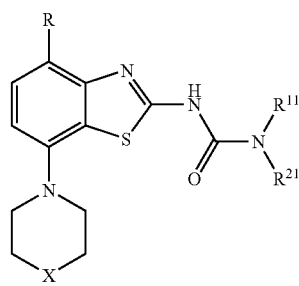

IA wherein
R is lower alkoxy or halogen;

R11 and R21, together with the N atom to which they are attached, form a heterocyclic ring, said heterocyclic ring being unsubstituted or substituted by lower alkyl, said heterocyclic ring being selected from the group consisting of
2-oxa-5-aza-bicyclo[2.2.1]heptane,
3-endo-hydroxy-8-aza-bicyclo[3.2.1]octane,
2-aza-bicyclo[2.2.2]octane,
1-oxo-2,8-diaza-spiro[4.5]decane,
3-aza-spiro[5.5]undecane,
8-aza-spiro[4.5]decane,
1-oxa-8-aza-spiro[4.5]decane,
1,8,8-trimethyl-3-aza-bicyclo[3.2.1]octane,
[1,4]oxazepane,
2-oxa-5-aza-bicyclo[2.2.2]octane,
8-oxa-3-aza-bicyclo[3.2.1]octane,
1,4-diaza-bicyclo[3.2.1]octane,
2-aza-bicyclo[2.2.1]heptane and
3-aza-bicyclo[3.2.1]octane, or
piperidin-1-yl, substituted by a substituent selected from the group —(CH$_2$)$_n$—NR'S(O)$_2$-lower alkyl, —C(O)NR'$_2$ and —(CH$_2$)$_n$-phenyl, said phenyl being unsubstituted or substituted by lower alkyl and R' is independently selected from hydrogen and lower alkyl;

X is —O— or CH$_2$—; and
n is 0, 1, 2, 3 or 4,
or a pharmaceutically acceptable acid addition salt thereof
The present invention also is directed to a novel compound of formula IB

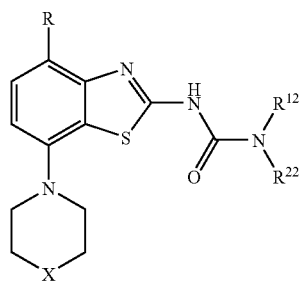

IB wherein
R is lower alkoxy or halogen;
R$^{12}$ is lower alkyl;
R$^{22}$ is cycloalkyl, substituted by one or two substituents, said substituents being selected from the group consisting of halogen, lower alkoxy and hydroxy; and
X is —O— or CH$_2$—; or a pharmaceutically acceptable salt thereof.

Novel compounds of formula IA, wherein X is —O—, are, for example, the following:
4-benzyl-4-hydroxymethyl-piperidine-1-carboxylic acid (4-methoxy-7-morpholin-4-yl-benzothiazol-2-yl)-amide,
3-aza-spiro[5.5]undecane-3-carboxylic acid (4-methoxy-7-morpholin-4-yl-benzothiazol-2-yl)-amide,
8-aza-spiro[4.5]decane-8-carboxylic acid (4-methoxy-7-morpholin-4-yl-benzothiazol-2-yl)-amide,
2-aza-bicyclo[2.2.2]octane-2-carboxylic acid (4-methoxy-7-morpholin-4-yl-benzothiazol-2-yl)-amide,
1-oxa-8-aza-spiro[4.5]decane-8-carboxylic acid (4-methoxy-7-morpholin-4-yl-benzothiazol-2-yl)-amide,
(R)-4-(1-hydroxy-ethyl)-piperidine-1-carboxylic acid (4-methoxy-7-morpholin-4-yl-benzothiazol-2-yl)-amide,
(S)-4-(1-hydroxy-ethyl)-piperidine-1-carboxylic acid (4-methoxy-7-morpholin-4-yl-benzothiazol-2-yl)-amide,
4-(methanesulfonylamino-methyl)-piperidine-1-carboxylic acid (4-methoxy-7-morpholin-4-yl-benzothiazol-2-yl)-amide,
piperidine-1,4-dicarboxylic acid 4-amide 1-[(4-methoxy-7-morpholin-4-yl-benzothiazol-2-yl)-amide],
(1R)-1,8,8-trimethyl-3-aza-bicyclo[3.2.1]octane-3-carboxylic acid (4-methoxy-7-morpholin-4-yl-benzothiazol-2-yl)-amide,
2-oxa-5-aza-bicyclo[2.2.2]octane-5-carboxylic acid (4-methoxy-7-morpholin-4-yl-benzothiazol-2-yl)-amide,
1,4-diaza-bicyclo[3.2.1]octane-4-carboxylic acid (4-methoxy-7-morpholin-4-yl-benzothiazol-2-yl)-amide or
(1S,4R)-2-aza-bicyclo[2.2.1]heptane-2-carboxylic acid (4-methoxy-7-morpholin-4-yl-benzothiazol-2-yl)-amide.

Novel compounds of formula IA are also those, wherein X is —CH$_2$, for example, the following:
1-oxa-8-aza-spiro[4.5]decane-8-carboxylic acid (4-methoxy-7-piperidin-1yl-benzothiazol-2-yl)-amide,
4-hydroxy-4-(4-methyl-benzyl)-piperidine-1-carboxylic acid (4-chloro-7-piperidin-1-yl-benzothiazol-2-yl)-amide or
4-benzyl-piperidine-1-carboxylic acid (4-chloro-7-piperidin-1-yl-benzothiazol-2-yl)-amide.

Novel compounds of formula IB, wherein X is —O—, are, for example, the following:
1-(4cis-fluoro-cyclohexyl)-3-(4-methoxy-7-morpholin-4-yl-benzothiazol-2-yl)-1-methyl-urea,
1-(4,4-difluoro-cyclohexyl)-3-(4-methoxy-7-morpholin-4-yl-benzothiazol-2-yl)-1-methyl-urea,
(cis)-1-(4-methoxy-cyclohexyl)-3-(4-methoxy-7-morpholin-4-yl-benzothiazol-2-yl)-1-methyl-urea,
(trans)-1-(4-hydroxy-cyclohexyl)-3-(4-methoxy-7-morpholin-4-yl-benzothiazol-2-yl)-1-methyl-urea,
(cis)-1-(4-hydroxy-cyclohexyl)-3-(4-methoxy-7-morpholin-4-yl-benzothiazol-2-yl)-1-methyl-urea or
(trans)-1-(4-methoxy-cyclohexyl)-3-(4-methoxy-7-morpholin-4-yl-benzothiazol-2-yl)-11-methyl-urea.

The present invention is also directed to the compounds of formula IA or IB as well as a process for the preparation of a compound of formula IA or IB.

The present invention also relates to a method of treatment for a disease modulated by the adenosine A$_2$ receptor comprising administering a therapeutically effective amount of a compound of formula I, IA or IB, or a pharmaceutically acceptable salts thereof, to a person in need of such treatment. Additionally, the present invention is related to a pharmaceutical composition comprising a compound of formula I, IA or IB, or a pharmaceutically acceptable salt thereof and a pharmaceutically inert carrier. Illnesses responsive to the modulation of the adenosine system include Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents for disorders such as coronary artery disease and heart failure. The most preferred indications in accordance with the present invention are those, which are based on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application for use against diseases, related to modulation of the the $A_{2a}$ receptor are compounds of formula I, wherein X is —O—, for example the following compounds:
(1S,4S)-2-oxa-5-aza-bicyclo[2.2.1]heptane-5-carboxylic acid (4-methoxy-7-morpholin-4-yl-benzothiazol-2-yl)-amide,
3-endo-hydroxy-8-aza-bicyclo[3.2.1]octane-8-carboxylic acid (4-methoxy-7-morpholin-4-yl-benzothiazol-2-yl)-amide,
2-methyl-1-oxo-2,8-diaza-spiro[4.5]decane-8-carboxylic acid (4-methoxy-7-morpholin-4-yl-benzothiazol-2-yl)-amide,
1-oxo-2,8-diaza-spiro[4.5]decane-8-carboxylic acid (4-methoxy-7-morpholin-4-yl-benzothiazol-2-yl)-amide,
4-benzyl-4-hydroxymethyl-piperidine-1-carboxylic acid (4-methoxy-7-morpholin-4-yl-benzothiazol-2-yl)-amide,
3-aza-spiro[5.5]undecane-3-carboxylic acid (4-methoxy-7-morpholin-4-yl-benzothiazol-2-yl)-amide,
8-aza-spiro[4.5]decane-8-carboxylic acid (4-methoxy-7-morpholin-4-yl-benzothiazol-2-yl)-amide,
2-aza-bicyclo[2.2.2]octane-2-carboxylic acid (4-methoxy-7-morpholin-4-yl-benzothiazol-2-yl)-amide,
1-oxa-8-aza-spiro[4.5]decane-8-carboxylic acid (4-methoxy-7-morpholin-4-yl-benzothiazol-2-yl)-amide,
(R)-4-(1-hydroxy-ethyl)-piperidine-1-carboxylic acid (4-methoxy-7-morpholin-4-yl-benzothiazol-2-yl)-amide,
(S)-4-(1-hydroxy-ethyl)-piperidine-1-carboxylic acid (4-methoxy-7-morpholin-4-yl-benzothiazol-2-yl)-amide,
4-(methanesulfonylamino-methyl)-piperidine-1-carboxylic acid (4-methoxy-7-morpholin-4-yl-benzothiazol-2-yl)-amide,
piperidine-1,4-dicarboxylic acid 4-amide 1-[(4-methoxy-7-morpholin-4-yl-benzothiazol-2-yl-amide],
1-(4-methoxy-7-morpholin-4-yl-benzothiazol-2-yl)-3-(tetrahydro-pyran-4-yl)-urea,
4-isopropyl-piperazine-1-carboxylic acid (4-methoxy-7-morpholin-4-yl-benzothiazol-2-yl)-amide,
4-phenyl-piperazine-1-carboxylic acid (4-methoxy-7-morpholin-4-yl-benzothiazol-2-yl)-amide,
1-cyclohexyl-3-(4-methoxy-7-morpholin-4-yl-benzothiazol-2-yl)-1-methyl-urea,
1-(4cis-fluoro-cyclohexyl)-3-(4-methoxy-7-morpholin-4-yl-benzothiazol-2-yl)-1-methyl-urea,
1-(4cis-fluoro-cyclohexyl)-3-(4-methoxy-7-morpholin-4-yl-benzothiazol-2-yl)-1-methyl-urea,
(cis)-1-(4-methoxy-cyclohexyl)-3-(4-methoxy-7-morpholin-4-yl-benzothiazol-2-yl)-1-methyl-urea,
(trans)-1-(4-hydroxy-cyclohexyl)-3-(4-methoxy-7-morpholin-4-yl-benzothiazol-2-yl)-1-methyl-urea,
[1,4]oxazepane-4-carboxylic acid (4-methoxy-7-morpholin-4-yl-benzothiazol-2-yl)-amide,
(cis)-1-(4-hydroxy-cyclohexyl)-3-(4-methoxy-7-morpholin-4-yl-benzothiazol-2-yl)-1-methyl-urea,
2-oxa-5-aza-bicyclo[2.2.2]octane-5-carboxylic acid (4-methoxy-7-morpholin-4-yl-benzothiazol-2-yl)-amide,
(trans)-1-(4-methoxy-cyclohexyl)-3-(4-methoxy-7-morpholin-4-yl-benzothiazol-2-yl)-1-methyl-urea,
(1S,4R)-2-aza-bicyclo[2.2.1]heptane-2-carboxylic acid (4-methoxy-7-morpholin-4-yl-benzothiazol-2-yl)-amide,
3-(4-methoxy-7-morpholin-4-yl-benzothiazol-2-yl)-1-methyl-1-(tetrahydro-pyran-4-yl)-urea,
1-cycloheptyl-3-(4-methoxy-7-morpholin-4-yl-benzothiazol-2-yl)-1-methyl-urea,
1-cyclopentyl-3-(4-methoxy-7-morpholin-4-yl-benzothiazol-2-yl)-1-methyl-urea andr
1-cyclopentyl-3-(4-methoxy-7-morpholin-4-yl-benzothiazol-2-yl)-urea.

Preferred compounds of formula I, wherein X is —CH$_2$— of the method of treatment of the present present invention against diseases, responsive to modulation of the $A_{2a}$ receptor are selected from the group consisting of
1-oxa-8-aza-spiro[4.5]decane-8-carboxylic acid (4-methoxy-7-piperidin-1yl-benzothiazol-2-yl)-amide,
4-hydroxy-4-(4-methyl-benzyl)-piperidine-1-carboxylic acid (4-chloro-7-piperidin-1-yl-benzothiazol-2-yl)-amide,
4-benzyl-piperidine-1-carboxylic acid (4-chloro-7-piperidin-1-yl-benzothiazol-2-yl)-amide,
4-methyl-3-oxo-piperazine-1-carboxylic acid (4-methoxy-7-piperidin-1-yl-benzothiazol-2-yl)-amide and
1-(4-chloro-7-piperidin-1-yl-benzothiazol-2-yl)-3-cyclohexyl-urea.

Compounds of formula IA or IB and or pharmaceutically acceptable salts thereof can be prepared by methods known to the art, for example, by processes described below, which process comprises
reacting a compound of formula (2)

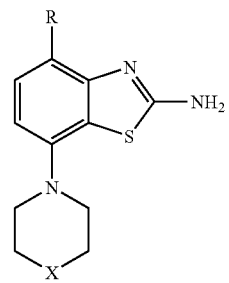

with phenyl chloroformate and then with a compound of formula

HNR$^{11}$R$^{21}$ (3A)

or

HNR$^{12}$R$^{22}$ (3B)

forming a compound of formula

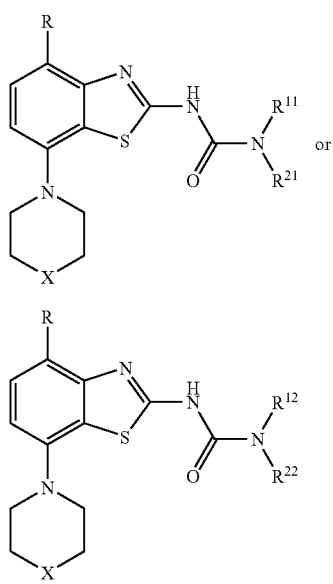

IA or

IB wherein R and X are as defined above, and R$^{11}$ and R$^{21}$ form together with the N atom to which they are attached heterocyclic rings, selected from the group consisting of 2-oxa-5-aza-bicyclo[2.2.1]heptane, 3-endo-hydroxy-8-aza-bicyclo[3.2.1]octane, 2-aza-bicyclo[2.2.2]octane, 1-oxo-2,8-diaza-spiro[4.5]decane, 3-aza-spiro[5.5]undecane, 8-aza-spiro[4.5]decane, 1-oxa-8-aza-spiro[4.5]decane, 1,8,8-trimethyl-3-aza-bicyclo[3.2.1]octane, [1,4]oxazepane, 2-oxa-5-aza-bicyclo[2.2.2]octane, 8-oxa-3-aza-bicyclo[3.2.1]octane, 1,4-diaza-bicyclo[3.2.1]octane, 2-aza-bicyclo[2.2.1]heptane or 3-aza-bicyclo[3.2.1]octane, and which rings may be unsubstituted or substituted by lower alkyl, or is selected from piperidin-1-yl, substituted by —(CH$_2$)$_n$-phenyl, —(CH$_2$)$_n$—NR'S(O)$_2$-lower alkyl, —C(O)NR'$_2$ or —(CH$_2$)$_n$-phenyl and wherein the phenyl ring is unsubstituted or substituted by lower alkyl and R' is hydrogen or lower alkyl, independently from each other in case R'$_2$ and n is described above, and R$^{12}$ is alkyl and R$^{22}$ is cycloalkyl, substituted by one or two substituents, wherein the substituents are selected from the group, consisting of halogen, lower alkoxy or hydroxy; or if desired, converting the compounds obtained into pharmaceutically acceptable acid addition salts.

The compounds of formula IA and IB may be prepared in accordance with process variant a) and with the following scheme 1. Scheme 2 shows the preparation of the intermediate compound of formula (2). 37 Examples are further described in more detail for the preparation of compounds of formula IA and IB.

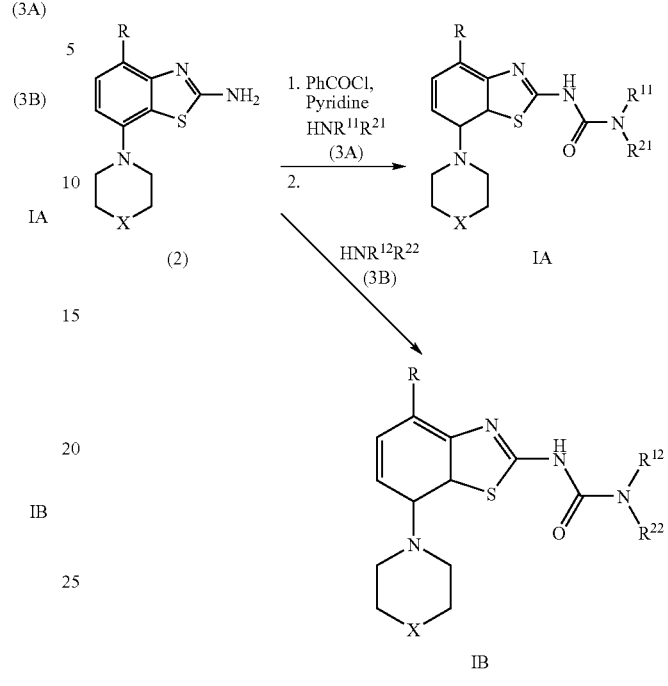

wherein the substitutents are described above.

Preparation of a Compound of Formula IA or IB

To a solution of a compound of formula (2), for example 4-methoxy-7-morpholin-4-yl-benzothiazol-2-yl-amine in dichloromethane is subsequently added pyridine and phenyl chloroformate and the resulting solution is stirred for 45 min at ambient temperature. Then a compound of formula (3A) or (3B), for example (1S,4S)-2-oxa-5-aza-bicyclo[2.2.1] heptane is added and the mixture stirred at ambient temperature for about 15 min and at 40° C. for 2.5 h. After cooling to ambient temperature, saturated aqueous sodium carbonate is added, the organic phase is separated and dryed.

The preparation of the starting compound of formula (2) has been described in EP 00113219.0 as follows:

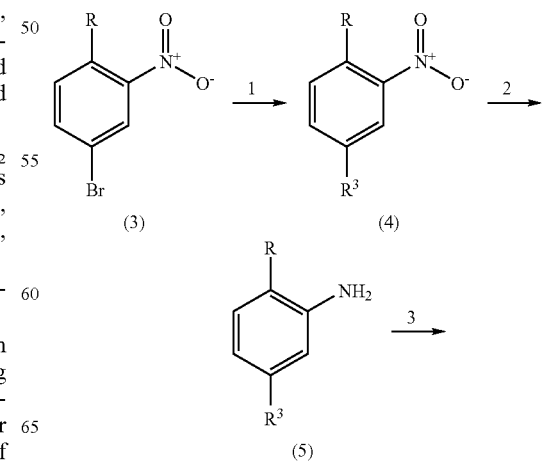

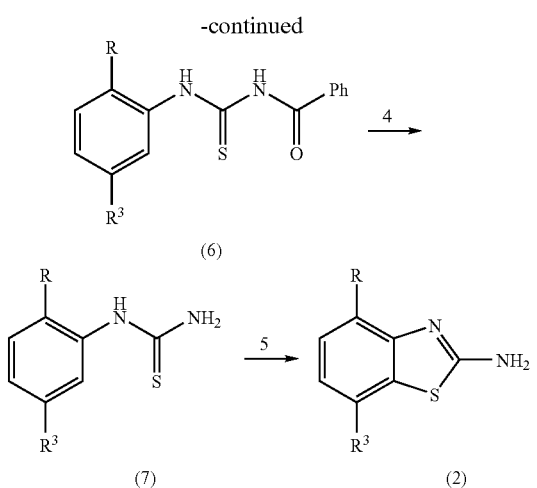

wherein the numbers 1–5 have the following meaning
1 morpholine or piperidine, base, Pd-catalyst,
2 $H_2$ and Pd—C, or $H_2$ and Raney-Ni, or $TiCl_3$, or Fe,
3 Ph(CO)NCS,
4 NaOMe,
5 $Br_2$.
R is alkoxy or halogen and $R^3$ is piperidin-1-yl or morpholinyl.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Pharmaceutically Acceptable Salts of Compounds of Formula IA or IB

The basic groups of compounds of formula IA or IB may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors.

The compounds of the invention were investigated in accordance with the following test.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values, the concentration where 50% of the non-specific binding is displaced, were calculated using a non-linear curve fitting program and Ki values calculated using the Cheng-Prussoff equation.

The preferred compounds of the invention have a pKi>7.5.

| Example No. | HA$_2$ (pKi) | Example No. | hA$_2$ (pKi) |
|---|---|---|---|
| 1 | 8.5 | 19 | 8.4 |
| 2 | 7.9 | 20 | 8.5 |
| 3 | 8.1 | 21 | 8.6 |
| 4 | 8.2 | 22 | 7.8 |
| 5 | 8.2 | 23 | 8.1 |
| 6 | 7.7 | 24 | 8.0 |
| 7 | 8.1 | 25 | 7.7 |
| 8 | 8.4 | 27 | 7.9 |
| 9 | 7.9 | 28 | 7.9 |
| 10 | 8.0 | 29 | 7.9 |
| 11 | 8.2 | 30 | 8.3 |
| 12 | 8.6 | 32 | 7.6 |
| 13 | 8.6 | 33 | 8.3 |
| 14 | 8.1 | 34 | 7.8 |
| 15 | 8.1 | 35 | 7.9 |
| 16 | 7.8 | 36 | 8.1 |
| 17 | 7.7 | 37 | 8.1 |
| 18 | 7.7 | | |

The compounds of formula I and the pharmaceutically acceptable salts of the compounds of formula I can be used to prepare pharmaceutical compositions. The pharmaceutical compositions of the invention can be administered orally, e.g. in the form of tablets, coated tablets, dragées, hard and soft gelatine capsules, solutions, emulsions or suspensions. The administration of the pharmaceutical compositions of the invention can, also be effected rectally, e.g. in the form of suppositories and parenterally, e.g. in the form of injection solutions.

A therapeutically effective amount of a compound of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical of the invention, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also relates to pharmaceutical compositions containing a therapeutically effective amount of a compound of formula I, including compounds of IA or IB, or a pharmaceutically acceptable salt thereof and a therapeutically inert carrier, The present invention also relates to a process for production of a pharmaceutical composition, which comprises bringing one or more compounds of formula I and/or pharmaceutically acceptable acid addition salts thereof and may also include one or more other therapeutically valuable substances into a galenical administration form together with one or more therapeutically inert carriers.

A method of treatment of the control or prevention of diseases based on the adenosine receptor antagonistic activity of the present invention comprises administering a therapeutically effective amount of a compound of formula I, including compounds of IA or IB, or a pharmaceutically acceptable salt thereof to a person in need of such treatment. Illnesses responsive to adenosine receptor antagonistic activity include Alzheimer's disease, Parkinson's disease, neuroprotection, schizophrenia, anxiety, pain, respiration deficits, depression, asthma, allergic responses, hypoxia, ischaemia, seizure and substance abuse. A compound of the present invention may be administered as a sedative, muscle relaxant, antipsychotic, antiepileptic, anticonvulsant and cardioprotective agent and for the production of pharmaceutical preparations.

The most preferred indications in accordance with the method of treatment of the present invention include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

(1S,4S)-2-Oxa-5-aza-bicyclo[2.2.1]heptane-5-carboxylic acid (4-methoxy-7-morpholin-4-yl-benzothiazol-2-yl)-amide To a solution of 4-methoxy-7-morpholin-4-yl-benzothiazol-2-ylamine (265 mg, 1.0 mmol) in dichloromethane (15 ml) is subsequently added pyridine (0.24 ml, 3.0 mmol) and phenyl chloroformate (0.15 ml, 1.2 mmol) and the resulting solution stirred for 45 min at ambient temperature. Then (1S,4S)-2-oxa-5-aza-bicyclo[2.2.1]heptane (490 mg, 3.6 mmol) is added and the mixture stirred at ambient temperature for 15 min and at 40° C. for 2.5 h. After cooling to ambient temperature, saturated aqueous sodium carbonate (15 ml) is added, the organic phase is separated, dried and the solvent evaporated in vacuo. Flash chromatography (silica, eluent: dichloromethane containing methanol (gradient from 0 to 5%)) afforded the title compound as white crystals (135 mg, 35% yield). MS: m/e=391(M+H$^+$).

Following the general method of example 1 the compounds of examples 2 to 37 were prepared as described.

EXAMPLE 2

1-(4-Methoxy-7-morpholin-4-yl-benzothiazol-2-yl)-3-(tetrahydro-pyran-4-yl)-urea

Using tetrahydro-pyran-4-yl-amine, the title compound was prepared as white crystals in 62% yield. MS: m/e=393 (M+H$^+$).

EXAMPLE 3

3-endo-Hydroxy-8-aza-bicyclo[3.2.1]octane-8-carboxylic acid (4-methoxy-7-morpholin-4-yl-benzothiazol-2-yl)-amide Using 8-aza-bicyclo[3.2.1]octan-3-endo-ol the title compound was prepared as white crystals in 49% yield. MS: m/e=419(M+H$^+$).

EXAMPLE 4

2-Methyl-1-oxo-2,8-diaza-spiro[4.5]decane-8-carboxylic acid (4-methoxy-7-morpholin-4-yl-benzothiazol-2-yl)-amide Using 4-spiro-[3-(N-methyl-2-pyrrolidinone)]piperidine, the title compound was prepared as white crystals in 43% yield. MS: m/e=460(M+H$^+$).

EXAMPLE 5

1-Oxo-2,8-diaza-spiro[4.5]decane-8-carboxylic acid (4-methoxy-7-morpholin-4-yl-benzothiazol-2-yl)-amide Using 4-spiro-[3-(2-pyrrolidinone)]piperidine, the title compound was prepared as white crystals in 40% yield. MS: m/e=446(M+H$^+$).

EXAMPLE 6

4-Isopropyl-piperazine-1-carboxylic acid (4-methoxy-7-morpholin-4-yl-benzothiazol-2-yl)-amide Using 1-(2-propyl)-piperazine, the title compound was prepared as white crystals in 62% yield. MS: m/e=420(M+H$^+$).

EXAMPLE 7

4-Phenyl-piperazine-1-carboxylic acid (4-methoxy-7-morpholin-4-yl-benzothiazol-2-yl)-amide Using 1-penyl-piperazine, the title compound was prepared as white crystals in 53% yield. MS: m/e=454(M+H$^+$).

EXAMPLE 8

4-Benzyl-4-hydroxymethyl-piperidine-1-carboxylic acid (4-methoxy-7-morpholin-4-yl-benzothiazol-2-yl)-amide Using (4-benzyl-piperidin-4-yl)-methanol, the title compound was prepared as light brown solid in 6% yield. MS: m/e=497(M+H$^+$).

EXAMPLE 9

1-Cyclohexyl-3-(4-methoxy-7-morpholin-4-yl-benzothiazol-2-yl)-1-methyl-urea

Using Cyclohexyl-methyl-amine, the title compound was prepared as white crystals in 73% yield. MS: m/e=405(M+H$^+$).

EXAMPLE 10

3-Aza-spiro[5.5]undecane-3-carboxylic acid (4-methoxy-7-morpholin-4-yl-benzothiazol-2-yl)-amide Using 3-aza-spiro[5.5]undecane, the title compound was prepared as white crystals in 38% yield. MS: m/e=445(M+H$^+$).

EXAMPLE 11

8-Aza-spiro[4.5]decane-8-carboxylic acid (4-methoxy-7-morpholin-4-yl-benzothiazol-2-yl)-amide Using 8-aza-spiro[4.5]decane, the title compound was prepared as white crystals in 48% yield. MS: m/e=431(M+H$^+$).

EXAMPLE 12

2-Aza-bicyclo[2.2.2]octane-2-carboxylic acid (4-methoxy-7-morpholin-4-yl-benzothiazol-2-yl)-amide Using 2-aza-bicyclo[2.2.2]octane, the title compound was prepared as white crystals in 47% yield. MS: m/e=403(M+H$^+$).

EXAMPLE 13

1-Oxa-8-aza-spiro[4.5]decane-8-carboxylic acid (4-methoxy-7-morpholin-4-yl-benzothiazol-2-yl)-amide Using 1-oxa-8-aza-spiro[4.5]decane, the title compound was prepared as white crystals in 40% yield. MS: m/e=433 (M+H$^+$).

EXAMPLE 14

(R)-4-(1-Hydroxy-ethyl)-piperidine-1-carboxylic acid (4-methoxy-7-morpholin-4-yl-benzothiazol-2-yl)-amide Using (R)-4-(1-hydroxy-ethyl)-piperidine, the title compound was prepared as white crystals in 21% yield. MS: m/e=421(M+H$^+$).

EXAMPLE 15

(S)-4-(1-Hydroxy-ethyl)-piperidine-1-carboxylic acid (4-methoxy-7-morpholin-4-yl-benzothiazol-2-yl)-amide Using (S)-4-(1-hydroxy-ethyl)-piperidine, the title compound was prepared as white crystals in 53% yield. MS: m/e=421(M+H$^+$).

EXAMPLE 16

4-(Methanesulfonylamino-methyl)-piperidine-1-carboxylic acid (4-methoxy-7-morpholin-4-yl-benzothiazol-2-yl)-amide Using piperidin-4-ylmethyl-carbamic acid tert-butyl ester, [1-(4-methoxy-7-morpholin-4-yl-benzothiazol-2-ylcarbamoyl)-piperidin-4-ylmethyl]-carbamic acid tert-butyl ester was prepared as white solid. Subsequent deprotection with trifluoroacetic acid and reaction with methanesulfonyl chloride/pyridine under standard conditions afforded the title compound as white crystals in 44% overall yield. MS: m/e=482([M−H$^+$]$^-$).

EXAMPLE 17

Piperidine-1,4-dicarboxylic acid 4-amide 1-[(4-methoxy-7-morpholin-4-yl-benzothiazol-2-yl)-amide]

Using piperidine-4-carboxylic acid amide, the title compound was prepared as white crystals in 44% yield. MS: m/e=420(M+H$^+$).

EXAMPLE 18

4-Methyl-3-oxo-piperazine-1-carboxylic acid (4-methoxy-7-piperidin-1-yl-benzothiazol-2-yl)-amide Using 4-methoxy-7-piperidin-1-yl-benzothiazol-2-ylamine and 4-methyl-3-oxo-piperazine, the title compound was prepared as yellow solid in 84% yield. MS: m/e=404 (M+H$^+$).

EXAMPLE 19

1-Oxa-8-aza-spiro[4.5]decane-8-carboxylic acid (4-methoxy-7-piperidin-1yl-benzothiazol-2-yl)-amide Using 4-methoxy-7-piperidin-1-yl-benzothiazol-2-ylamine and 1-oxa-8-aza-spiro[4.5]decane, the title compound was prepared as beige crystals in 52% yield. MS: m/e=431(M+H$^+$).

EXAMPLE 20

4-Hydroxy-4-(4-methyl-benzyl)-piperidine-1-carboxylic acid (4-chloro-7-piperidin-1-yl-benzothiazol-2-yl)-amide Using 4-chloro-7-piperidin-1-yl-benzothiazol-2-ylamine and 4-hydroxy-4-(4-methylbenzyl)-piperidine, the title compound was prepared as white solid in 70% yield. MS: m/e=431(M+H$^+$).

EXAMPLE 21

1-(4-Chloro-7-piperidin-1-yl-benzothiazol-2-yl)-3-cyclohexyl-urea

Using 4-chloro-7-piperidin-1-yl-benzothiazol-2-ylamine and cyclohexylamine, the title compound was prepared as white solid in 73% yield. MS 394(M+H$^+$).

EXAMPLE 22

4-Benzyl-piperidine-1-carboxylic acid (4-chloro-7-piperidin-1-yl-benzothiazol-2-yl)-amide Using 4-chloro-7-piperidin-1-yl-benzothiazol-2-ylamine and 4-benzylpiperidine, the title compound was prepared as white solid in 80% yield. MS 470(M+H$^+$).

EXAMPLE 23

1-(4cis-Fluoro-cyclohexyl)-3-(4-methoxy-7-morpholin-4-yl-benzothiazol-2-yl)-1-methyl-urea Using (cis)-(4-fluoro-cyclohexyl)-methyl-amine the title compound was prepared as white crystals (yield 24%), mp 201–204° C. MS: m/e=423 (M+H$^+$).

EXAMPLE 24

1-(4,4-Difluoro-cyclohexyl)-3-(4-methoxy-7-morpholin-4-yl-benzothiazol-2-yl)-1-methyl-urea Using (4,4-difluoro-cyclohexyl)-methyl-amine the title compound was prepared as white crystals (yield 44%), mp 189–192° C. MS: m/e=441(M+H$^+$).

EXAMPLE 25

(cis)-1-(4-Methoxy-cyclohexyl)-3-(4-methoxy-7-morpholin-4-yl-benzothiazol-2-yl)-1-methyl-urea Using (cis)-(4-methoxy-cyclohexyl)-methyl-amine the title compound was prepared as white crystals (yield 39%), mp 198–200° C. MS: m/e=435 (M+H$^+$).

EXAMPLE 26

(1R)-1,8,8-Trimethyl-3-aza-bicyclo[3.2.1]octane-3-carboxylic acid (4-methoxy-7-morpholin-4-yl-benzothiazol-2-yl)-amide Using camphidine the title compound was prepared as white crystals (yield 75%), mp 185–189° C. MS: m/e=445 (M+H$^+$).

EXAMPLE 27

(trans)-1-(4-Hydroxy-cyclohexyl)-3-(4-methoxy-7-morpholin-4-yl-benzothiazol-2-yl)-1-methyl-urea Using (trans)-(4-hydroxy-cyclohexyl)-methyl-amine the title compound was prepared as off-white solid (yield 44%), mp 158–162° C. MS: m/e=421 (M+H$^+$).

EXAMPLE 28

Oxazepane-4-carboxylic acid (4-methoxy-7-morpholin-4-yl-benzothiazol-2-yl)-amide Using [1,4]oxazepane the title compound was prepared as light-yellow solid (yield 57%), mp 171–172° C. MS: m/e=393 (M+H$^+$).

EXAMPLE 29

(cis)-1-(4-Hydroxy-cyclohexyl)-3-(4-methoxy-7-morpholin-4-yl-benzothiazol-2-yl)-1-methyl-urea Using (cis)-(4-hydroxy-cyclohexyl)-methyl-amine the title compound was prepared as white solid (yield 66%), mp 169–171° C. MS: m/e=421 (M+H$^+$).

EXAMPLE 30

2-Oxa-5-aza-bicyclo[2.2.2]octane-5-carboxylic acid (4-methoxy-7-morpholin-4-yl-benzothiazol-2-yl)-amide Using 2-oxa-5-aza-bizyclo[2.2.2]octane the title compound was prepared as white solid (yield 69%), mp 164–170° C. MS: m/e=405 (M+H$^+$).

EXAMPLE 31

1,4-Diaza-bicyclo[3.2.1]octane-4-carboxylic acid (4-methoxy-7-morpholin-4-yl-benzothiazol-2-yl)-amide Using 1,4-diaza-bicyclo[3.2.1]octane the title compound was prepared as light-yellow crystals (yield 51%). MS: m/e=404 (M+H$^+$).

EXAMPLE 32

(trans)-1-(4-Methoxy-cyclohexyl)-3-(4-methoxy-7-morpholin-4-yl-benzothiazol-2-yl)-1-methyl-urea Using (trans)-(4-methoxy-cyclohexyl)-methyl-amine the title compound was prepared as white solid (yield 48%), mp 211–213° C. MS: m/e=435 (M+H$^+$).

EXAMPLE 33

(1S,4R)-2-Aza-bicyclo[2.2.1]heptane-2-carboxylic acid (4-methoxy-7-morpholin-4-yl-benzothiazol-2-yl)-amide Using (1S,4R)-2-aza-bicyclo[2.2.1]heptane the title compound was prepared as white crystals (yield 67%), mp 149° C. MS: m/e=389 (M+H$^+$).

EXAMPLE 34

3-(4-Methoxy-7-morpholin-4-yl-benzothiazol-2-yl)-1-methyl-1-(tetrahydro-pyran-4-yl)-urea Using (4-tetrahydropyranyl)-methyl-amine the title compound was prepared as white solid (yield 56%), mp 240–242° C. MS: m/e=407 (M+H$^+$).

EXAMPLE 35

1-Cycloheptyl-3-(4-methoxy-7-morpholin-4-yl-benzothiazol-2-yl)-1-methyl-urea

Using cycloheptyl-methyl-amine the title compound was prepared as white solid (yield 70%), mp 198–200° C. MS: m/e=419 (M+H$^+$).

EXAMPLE 36

1-Cyclopentyl-3-(4-methoxy-7-morpholin-4-yl-benzothiazol-2-yl)-1-methyl-urea

Using cyclopentyl-methyl-amine the title compound was prepared as white solid (yield 48%), mp 110–125° C. MS: m/e=391 (M+H$^+$).

EXAMPLE 37

1-Cyclopentyl-3-(4-methoxy-7-morpholin-4-yl-benzothiazol-2-yl)-urea

Using cyclopentylamine the tide compound was prepared as white crystals (yield 57%), mp 191–194° C. MS: m/e=377 (M+H$^+$).

Preparation of Intermediates for Examples 1 to 22

EXAMPLE 38

4-Benzyl-4-hydroxymethyl-piperidine 1,4-Dibenzyl-4-hydroxymethyl-piperidine (1.0 g, 3.4 mmol) in dichloromethane (20 ml) are treated with 1-chloroethyl-chloroformate (0.48 ml, 4.3 mmol, dissolved in 1.5 ml dichloromethane) and the resulting solution is stirred at 0° C. for 30 min. The solvent is removed in vacuo and the resulting residue refluxed in methanol (20 ml) for 40 min. After removal of the volatile components in vacuo, the title compound is isolated by flash chromatography (silca, eluent dichloromethane/methanol/triethylamine (9:1:0.1, then 4:1:0.1 followed by 3:1:0.1)) as a brown resin in 40% yield. MS 206(M+H$^+$).

EXAMPLE 39

1,4-Dibenzyl-4-hydroxymethyl-piperidine

Was prepared from 1,4-dibenzyl-piperidine-4-carboxylic acid ethyl ester (*J. Chem. Soc., Perkin Trans*. 1 1996, 20, 2545–2551.) by lithium aluminium hydride reduction in tetrahydrofurane under standard conditions in 81% yield. MS 296(M+H$^+$).

EXAMPLE 40

3-Aza-spiro[5.5]undecane

Was prepared from (3,3-tetramethylenglutarimide by lithium aluminium hydride reduction in tetrahydrofurane under standard conditions. Flash chromatography (silica, eluent dichloromethane/methanol/triethylamine 10:2:0.1) afforded the title compound as colorless oil (94% yield). MS 140(M+H$^+$).

EXAMPLE 41

8-Aza-spiro[4.5]decane

Was prepared from (3,3-pentamethylenglutarimide by lithium aluminium hydride reduction in tetrahydrofurane under standard conditions. Flash chromatography (silica, eluent dichloromethane/methanol/triethylamine 10:2:0.1) afforded the title compound as light yellow oil (>95% yield). MS 154(M+H$^+$).

EXAMPLE 42

(trans)-(4-hydroxy-cyclohexyl)-methyl-amine

The title compound was prepared from (trans)-(4-hydroxy-cyclohexyl)-amine by reaction with di-tert.-butyl dicarbonate in aqueous sodium hydroxide under standard conditions and subsequent reduction with lithium aluminum hydride in THF under standard conditions.

If not described differently, the other N-methylated amines were prepared in the same manner.

EXAMPLE 43

(cis)-(4-fluoro-cylohexyl)-methyl-amine

The title compound was prepared from (cis)-(4-fluorocyclohexyl)-carbamic acid benzyl ester by lithium aluminum hydride reduction under standard conditions in 91% yield.

EXAMPLE 44

(cis)-(4-fluoro-cyclohexyl)-carbamic acid benzyl ester (trans)-(4-hydroxy-cyclohexyl)-carbamic acid benzyl ester (900 mg, 3.6 mmol) are dissolved in dichloromethane (30 ml) and treated with diethylamino-sulfurtrifluoride (1 ml, 7.2 mmol). After 1 ha at room temperature, 5% aqueous sodium hydrogen carbonate (15.3 g, 7.2 mmol) are added and stirring continued for another hour. The layers are separated, the aqueous phase is extracted twice with each 20 ml of dichloromethane, the combined organic layers are dried with magnesium sulfate and evaporated. Flash chromatography (silica, hexane containing 0 to 30% ethyl acetate) afforded the title compound as light-yellow crystals (yield 14%), mp 105–107° C. MS: m/e=252 (M+H$^+$).

EXAMPLE 45

(4,4-difluoro-cyclohexyl)-methyl-amine

The title compound was prepared from 4,4-difluorocyclohexanone (prepared from 8,8-Difluoro-1,4-dioxa-spiro[4.5]decane by deprotection with sulfuric acid under standard conditions) and methylamine by reductive amination under standard conditions (Pd hydroxide in methanol, 1 atm hydrogen) in ~50% yield. Recrystallization of the hydrochloride from ethanol/diethylether afforded analytical pure material. Light-brown solid, mp 137–144° C. MS: m/e=186 (M+H$^+$).

EXAMPLE 46

8,8-Difluoro-1,4-dioxa-spiro[4.5]decane 1,4-Dioxa-spiro[4.5]decan-8-one (9.0 g, 56 mmol) and (diethylamino)sulfur trifluoride (19 g, 112 mmol) are reacted in dichloromethane (180 ml) for 2 h at room temperature. The mixture is poured in water (300 ml), the layers are separated and the aqueous phase back-extracted twice with dichloromethane (50 ml). The combined organic phases are dried with magnesium sulfate and evaporated. Distillation under reduced pressure over a vigreux-column afforded the title compound as colorless liquid (6.0 g, 60%), bp 65–72° C. at 13–14 mbar, MS: m/e=186 (M$^+$), contaminated with ~30% 8-Fluoro-1,4-dioxa-spiro[4.5]dec-7-ene, MS: m/e=158 (M$^+$).

EXAMPLE 47

2-oxa-5-aza-bicyclo[2.2.2]octane

The title compound was prepared from 2-oxa-5-azabicyclo[2.2.2]octan-6-one (*J. Polymer Sci.* 1990, 28, 3251–60) by lithium aluminum hydride reduction under standard conditions in 84% yield. MS: m/e=113 (M$^+$).

EXAMPLE 48

1,4-Diaza-bicyclo[3.2.1]octane

Was prepared according to the procedure published in U.S. Pat. No. 3,954,766 (1976). MS: m/e=112 (M$^+$).

EXAMPLE 49

(1S,4R)-2-Aza-bicyclo[2.2.1]heptane

The title compound was prepared from (1S,4R)-2-azabicyclo[2.2.1]heptan-3-one by lithium aluminum hydride reduction under standard conditions in 88% yield. MS: m/e=97 (M$^+$).

The invention claimed is:
1. A compound of formula

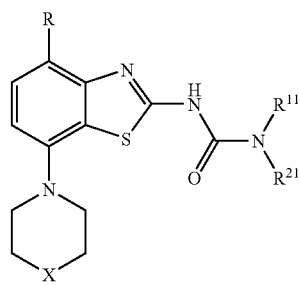

IA wherein
R is lower alkoxy or halogen;
R$^{11}$ and R$^{21}$, together with the N atom to which they are attached, form a heterocyclic ring, said heterocyclic ring being unsubstituted or substituted by lower alkyl, selected from the group consisting of
2-oxa-5-aza-bicyclo[2.2.1]heptane,
3-endo-hydroxy-8-aza-bicyclo[3.2.1]octane,
2-aza-bicyclo[2.2.2]octane,
1-oxo-2,8-diaza-spiro[4.5]decane,
3-aza-spiro[5.5]undecane, 8-aza-spiro[4.5]decane,
1-oxa-8-aza-spiro[4.5]decane,
1,8,8-trimethyl-3-aza-bicyclo[3.2.1]octane,
[1,4]oxazepane,
2-oxa-5-aza-bicyclo[2.2.2]octane,
8-oxa-3-aza-bicyclo[3.2.1]octane,
1,4-diaza-bicyclo[3.2.1]octane,
2-aza-bicyclo[2.2.1]heptane and
3-aza-bicyclo[3.2.1]octane, or
piperidin-1-yl, substituted by a substituent selected from the group —(CH$_2$)$_n$—NR'S(O)$_2$-lower alkyl, —C(O)NR'$_2$ and —(CH$_2$)$_n$-phenyl, said phenyl ring being unsubstituted or substituted by lower alkyl, and R' being independently selected from hydrogen and lower alkyl;

X is —CH$_2$—; and n is 0, 1, 2, 3 or 4;

or a pharmaceutically acceptable acid addition salt thereof.

2. The compound of formula IA according to claim 1, wherein the compound is selected from the group consisting of 1-oxa-8-aza-spiro[4.5]decane-8-carboxylic acid (4-methoxy-7-piperidin-1yl-benzothiazol-2-yl)-amide, 4-hydroxy-4-(4-methyl-benzyl)-piperidine-1-carboxylic acid (4-chloro-7-piperidin-1-yl-benzothiazol-2-yl)-amide and 4-benzyl-piperidine-1-carboxylic acid (4-chloro-7-piperidin-1-yl-benzothiazol-2-yl)-amide.

3. A process for preparing a compound of formula IA as defined in claim 1 comprising reacting a compound of formula

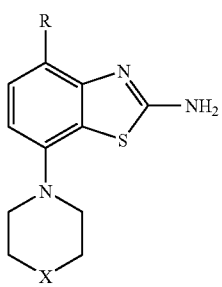

(2)

with phenyl chloroformate and then with a compound of formula

HNR$^{11}$R$^{21}$ (3A)

forming a compound of formula

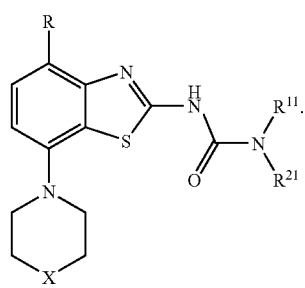

IA

4. A pharmaceutical composition comprising a compound of formula IA according to claim 1, or a pharmaceutically acceptable salt thereof; and a pharmaceutically inert carrier.

5. A compound of formula

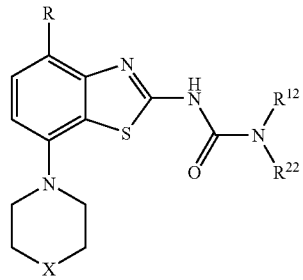

IB wherein

R is lower alkoxy or halogen;

R$^{12}$ is lower alkyl and

R$^{22}$ is cycloalkyl, substituted by one or two substituents, selected from the group consisting of halogen, lower alkoxy or hydroxy; and X is —O— or CH$_2$—;

or a pharmaceutically acceptable acid addition salt thereof.

6. The compound of formula IB according to claim 5, wherein X is —O—.

7. The compound of formula IB according to claim 6, wherein the compound is selected from the group consisting of 1-(4cis-fluoro-cyclohexyl)-3-(4-methoxy-7-morpholin-4-yl-benzothiazol-2-yl)-1-methyl-urea, 1-(4,4-difluoro-cyclohexyl)-3-(4-methoxy-7-morpholin-4-yl-benzothiazol-2-yl)-1-methyl-urea, (cis)-1-(4-methoxy-cyclohexyl)-3-(4-methoxy-7-morpholin-4-yl-benzothiazol-2-yl)-1-methyl-urea, (trans)-1-(4-hydroxy-cyclohexyl)-3-(4-methoxy-7-morpholin-4-yl-benzothiazol-2-yl)-1-methyl-urea, (cis)-1-(4-hydroxy-cyclohexyl)-3-(4-methoxy-7-morpholin-4-yl-benzothiazol-2-yl)-11-methyl-urea and (trans)-1-(4-methoxy-cyclohexyl)-3-(4-methoxy-7-morpholin-4-yl-benzothiazol-2-yl)-1-methyl-urea.

8. A process for preparing a compound of formula IB comprising reaction of a compound of formula

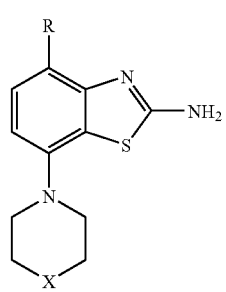

(2)

with phenyl chloroformate and then with a compound of formula

HNR$^{12}$R$^{22}$ (3B)

forming a compound of formula

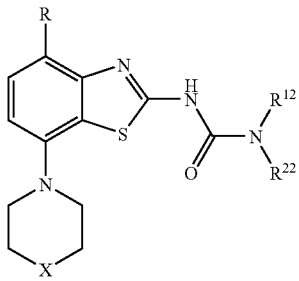

IB wherein R is lower alkoxy or halogen;
X is —O— or $CH_2$—;
$R^{12}$ is alkyl; and
$R^{22}$ is cycloalkyl, substituted by one or two substituents selected from the group consisting of halogen, lower alkoxy and hydroxy.

9. A pharmaceutical composition comprising a compound of formula IB according to claim 5 or a pharmaceutically acceptable salt thereof and a pharmaceutically inert carrier.

* * * * *

UNITED STATES PATENT AND TRADEMARK OFFICE
CERTIFICATE OF CORRECTION

PATENT NO.        : 7,019,001 B2
APPLICATION NO.   : 10/691770
DATED             : March 28, 2006
INVENTOR(S)       : Flohr et al.

Page 1 of 1

It is certified that error appears in the above-identified patent and that said Letters Patent is hereby corrected as shown below:

TITLE PAGE:

• On the Title page the Assignee information reads "(73) Assignee: Hoffman-La Roche Inc., Nutley, NJ (US)".
The Assignee information should read
-- (73) Assignee: Hoffmann-La Roche Inc., Nutley, NJ (US) --.

Signed and Sealed this

Seventeenth Day of October, 2006

JON W. DUDAS
*Director of the United States Patent and Trademark Office*